(12) United States Patent
Hovey

(10) Patent No.: US 10,231,885 B2
(45) Date of Patent: Mar. 19, 2019

(54) PROTECTIVE UNDERGARMENT

(71) Applicant: Glenna Rae Hovey, Hopkins, MN (US)

(72) Inventor: Glenna Rae Hovey, Hopkins, MN (US)

(*) Notice: Subject to any disclaimer, the term of this patent is extended or adjusted under 35 U.S.C. 154(b) by 1061 days.

(21) Appl. No.: 14/558,053

(22) Filed: Dec. 2, 2014

(65) Prior Publication Data
US 2015/0157513 A1 Jun. 11, 2015

Related U.S. Application Data

(60) Provisional application No. 61/913,113, filed on Dec. 6, 2013.

(51) Int. Cl.
*A61F 13/15* (2006.01)
*A61F 13/49* (2006.01)
*A61F 13/505* (2006.01)

(52) U.S. Cl.
CPC ...... *A61F 13/49006* (2013.01); *A61F 13/505* (2013.01); *A61F 13/15268* (2013.01); *A61F 2013/15276* (2013.01); *A61F 2013/5055* (2013.01)

(58) Field of Classification Search
CPC .............. A61F 13/505; A61F 13/49066; A61F 13/15268; A61F 2013/5055; A61F 2013/15276
USPC ......... 604/385.14, 385.15, 385.11, 395, 393, 604/400
See application file for complete search history.

(56) References Cited

U.S. PATENT DOCUMENTS

| | | | |
|---|---|---|---|
| 2,711,735 A | 6/1955 | Sabo | |
| 4,555,245 A | 11/1985 | Armbruster | |
| 4,695,279 A | 9/1987 | Steer | |
| 4,880,424 A | 11/1989 | Rautenberg | |
| 4,923,454 A | 5/1990 | Seymour et al. | |
| 5,098,419 A | 3/1992 | Gold | |
| D463,091 S | 9/2002 | Lydell | |
| 6,756,076 B2 | 6/2004 | Brier | |
| 6,807,685 B1 | 10/2004 | Hasegawa et al. | |
| 7,322,966 B1 | 1/2008 | Deerin | |
| 7,951,128 B1 | 5/2011 | Lewis | |
| 8,117,675 B2 | 2/2012 | Strange et al. | |
| 8,123,735 B2 | 2/2012 | Deerin | |
| 2002/0035747 A1 | 3/2002 | Kusibojoska et al. | |
| 2005/0065494 A1 | 3/2005 | Harriott | |
| 2005/0131382 A1* | 6/2005 | Brud ............... | A61F 13/496 604/401 |

(Continued)

OTHER PUBLICATIONS

Salk "HealthDri Men's and Women's Fashionable Incontinence Briefs and Panties", retrieved Nov. 9, 2014: http://www.healthdri.com/healthdri.html.

(Continued)

*Primary Examiner* — Jacqueline Stephens
(74) *Attorney, Agent, or Firm* — Merchant & Gould P.C.

(57) ABSTRACT

An undergarment configured to help absorb leaks of bodily fluids from a person suffering from mild to moderate incontinence or other conditions includes a main body made of a material that allows the absorption of bodily fluids and a crotch piece made of a material that allows the absorption of bodily fluids that overlays the crotch portion of the main body. The crotch piece of the undergarment can extend high enough and be wide enough on the front side of the garment's main body so as to offer an adequate area of protection to the user.

16 Claims, 6 Drawing Sheets

(56) References Cited

U.S. PATENT DOCUMENTS

| | | |
|---|---|---|
| 2008/0114327 A1 | 5/2008 | Barge |
| 2010/0249736 A1 | 9/2010 | Png et al. |
| 2011/0224639 A1 | 9/2011 | Venable |
| 2012/0046632 A1 | 2/2012 | Malowaniec |
| 2014/0025027 A1 | 1/2014 | Png et al. |
| 2014/0039432 A1 | 2/2014 | Dunbar et al. |

OTHER PUBLICATIONS

THINX "Change Your Underwear Change the World" http://www.shethinx.com/collections/, retrieved Nov. 9, 2014.
THINX "the Smartest Underwear in your Drawer" http://www.shethinx.com/technology/, retrieved Nov. 9, 2014.
THINX "Change Your Underwear Change the World" http://www.shethinx.com/, retrieved Nov. 9, 2014.

* cited by examiner

PROTECTIVE UNDERGARMENT

CROSS REFERENCE TO RELATED APPLICATIONS

The present application claims the benefit of U.S. Provisional Application No. 61/913,113, filed Dec. 6, 2013, which is incorporated herein by reference.

FIELD OF INVENTION

The present disclosure relates to the field of undergarments. More specifically, the disclosure relates to undergarments worn by individuals experiencing mild to moderate incontinence or experiencing spotting of urine or menstrual blood. This disclosure relates to undergarments with one or more crotch pieces that can absorb bodily fluids.

BACKGROUND

Involuntary leakage of bodily fluids such as urine or menstrual blood is a common problem. The leakage can be due to urinary incontinence (also known as enuresis) or menstruation. Devices for helping absorb bodily fluids can come in different forms including pantiliners, sanitary napkins, incontinence pads, disposable diapers, and incontinence underwear. Incontinence undergarments are typically used by individuals suffering from mild to severe incontinence. However, existing incontinence underwear is often uncomfortably bulky, includes materials that create audible noises when the user moves, and/or causes inconvenience or expense for the user because of the need to dispose of the undergarment after a single use, or having to remove pieces of the underwear (e.g., additional pads or liners) for disposal or washing. For these reasons, persons with mild incontinence often rely on disposable pantiliners.

Previous attempts at designing incontinence underwear fail to eliminate one or more of the inconveniences associated with incontinence underwear or pads. The previous attempts try to better contour to a user's body, prevent leakage of bodily fluids, and create a better area for a sanitary napkin to be placed in order to bring about more comfort to the user. Although these incontinence undergarments can absorb bodily fluids, they need to be disposed of after a single use, are made of uncomfortable materials that are bulky and/or generate embarrassing noises, and/or do not cater to a wide variety of bodily shapes and sizes. Another flaw with existing designs is spotting or leaking of bodily fluid not adequately absorbed by a user's undergarment. This leak or spot may occur because the incontinence protection area is too small or is incorrectly positioned, often not extending far enough up the front of the garment.

Underwear with a sewn double paneled crotch exists. This double paneled crotch rests under the user's body when worn and is designed to catch bodily leaks or spotting. However, the existing designs' double paneled crotch does not catch all spotting or leakage. Thus a spot can land on the single layered "main" body of the underwear. This problem allows the spot of fluid to more easily penetrate through the underwear and onto, or through, the pants, slacks, jeans, dress, or various other outer garments the person is wearing. This penetration of bodily fluid can be uncomfortable, unpleasant, and embarrassing to the wearer.

It would be beneficial to provide for a protective undergarment that is comfortable, inconspicuous, and prevents leakage caused by mild to moderate incontinence or menstrual bleeding. It would further be beneficial to provide for a protective undergarment that is constructed of natural materials and is non-bulky and quiet.

SUMMARY

The present disclosure provides undergarments that are designed to overcome one or more drawbacks of prior devices. The undergarments discussed herein can provide a non-disposable undergarment which gives a user comfort and adequate protection from leaking or spotting. The present disclosure may allow the user to wear incontinence underwear without the risk of embarrassing noise and without the bunching or bundling of the incontinence undergarment beneath the user's clothes, while still offering protection from mild to moderate incontinence. Accordingly, a need exists for protective undergarments that adequately protect a user, are comfortable to wear, and can be laundered after use. Another need exists for such an undergarment which is particularly adapted for various body shapes and sizes. Yet another need exists for protective undergarments whose area of protection is large enough to prevent leaks which commonly occur above the front seam of the crotch area of a typical undergarment. Yet another need exists for a non-disposable protective undergarment which offers the user comfort, does not produce embarrassing noise, is made to fit varying body shapes and sizes, and has a double or multi layered crotch portion with an area large enough to catch the spotting and leakage that would typically occur during incontinence.

In accomplishing the above, the present disclosure provides an undergarment including a main body with two leg holes, a front side and a back side that meet at a bottom center fold line, a holding portion comprising an upper portion of the front side and an upper portion of the back side, a crotch portion resting between the two leg holes and bridging the upper portions of the front side and the back side, and a rear connecting line defining a back end of the crotch portion. A crotch piece rests at least partially on the crotch portion, and is at least partially connected to the crotch portion of the main body at the rear connecting line. The crotch piece extends from the rear connecting line to the front side, extending a part of the way onto the upper portion of the front side. The crotch piece is constructed of an absorbent material and is substantially free of plastic materials.

In one or more embodiments, an undergarment can include a main body, the main body having two leg holes, a rear connecting line, a holding portion and a crotch portion, and a crotch piece that rests partially between the leg holes. The crotch piece can be attached onto the outer side (i.e. the side away from the wearer's body) of the main body and can be at least partially connected to the crotch portion of the main body at the rear connecting line. The crotch piece may comprise multiple layers.

These features of novelty and various other advantages that characterize the invention are pointed out with particularity in the claims annexed hereto and forming a part hereof. However, for a better understanding of the invention, its advantages, and the objects obtained by its use, reference should be made to the drawings that form a further part of this disclosure, and to the accompanying descriptive matter, in which there is illustrated and described a preferred embodiment of the invention.

Figure 1:
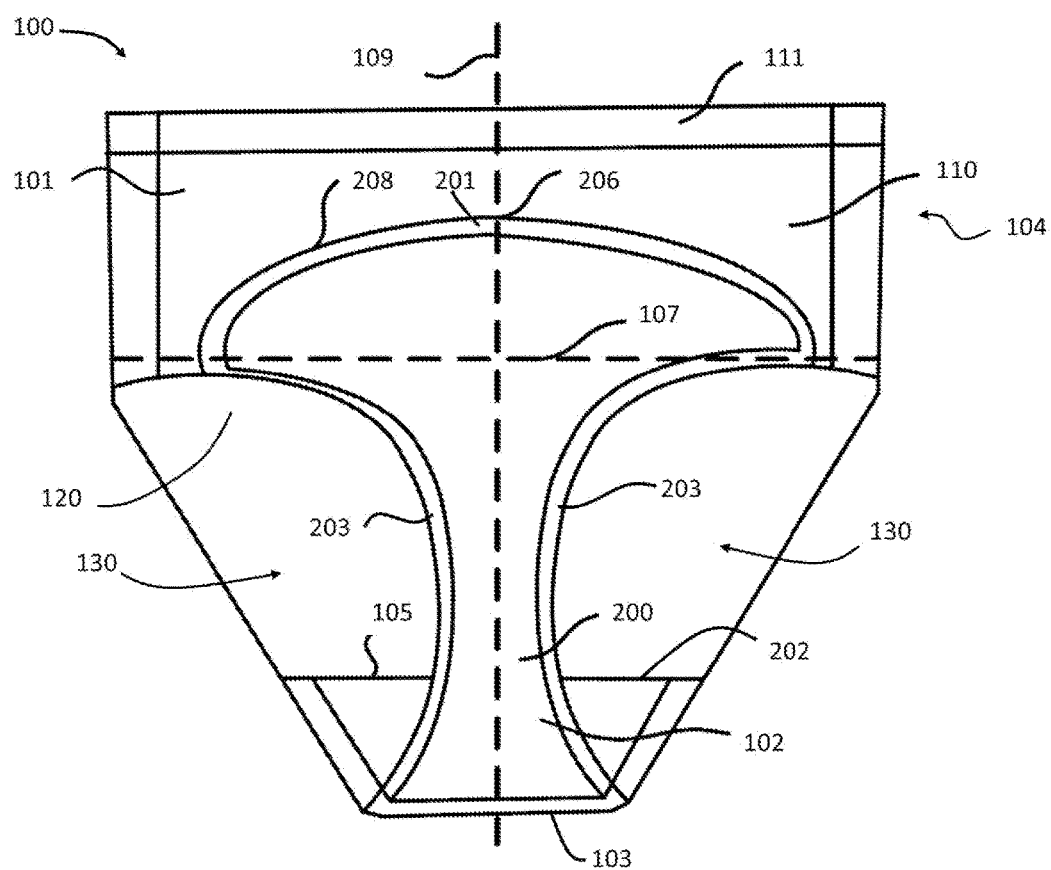
FIG. 1 shows a front view of an example of an incontinence undergarment.

While the disclosure is amenable to various modifications or alternative forms, specifics thereof have been shown by way of example in the drawings and will be described in detail. It should be understood however, that the disclosure is not limited to the particular embodiments described. On the contrary, the disclosure is to cover all modifications, equivalents, or alternatives thereof.

DETAILED DESCRIPTION

Advantages and embodiments of this disclosure are illustrated by the following examples, but the particular materials and amounts recited in these examples, as well as other conditions and details, should not be construed to unduly limit this disclosure. The apparatuses disclosed herein may be used to provide protection to a person suffering from mild to moderate incontinence. While not meant to be limiting, the systems are illustrated using knit fabric. It will be appreciated that the apparatuses can be made from or to include other materials.

According to an embodiment, the undergarment includes a main body and a crotch portion comprising a crotch piece constructed of absorbent materials. The undergarment is constructed to be comfortable, non-bulky, machine washable and reusable, quiet and inconspicuous, while being capable of absorbing bodily fluids due to mild to moderate incontinence or menstrual flow. The terms underwear, undergarment, incontinence undergarment, incontinence underwear, panty, and underpants are used here interchangeably.

According to an embodiment, the undergarment can include a main body that includes two leg holes, a front side and a back side separated by a bottom center fold line, a holding portion comprising an upper portion of the front side and an upper portion of the back side, a crotch portion resting between the two leg holes and bridging the upper portions of the front side and the back side, where a rear connecting line defines the back end of the crotch portion. A crotch piece rests at least partially on the crotch portion, and is connected to the crotch portion at the rear connecting line. The crotch piece extends from the rear connecting line to the front side, extending at least part of the way up the front side.

FIG. 1 is a schematic front view diagram showing components of an undergarment 100 according to embodiments of the present disclosure. The undergarment 100 can include a main body 101 comprising a crotch portion 102, a holding portion 104, and a rear connecting line 105; and a crotch piece 200. The main body 101 comprises a front side 110 and a back side 120, and an upper portion consisting of an upper portion of the front 111 and an upper portion of the back 121. The upper portions 111, 121 are defined as the portion of the main body 101 that is approximately above the line 107 in FIG. 1. The holding portion 104 is defined by the upper portions 111, 121, and can be configured to secure the undergarment 100 to the user, such at or around the abdominal region. In the embodiments, the holding portion 104 is a cylindrical piece of fabric constructed from one or more pieces of fabric. The holding portion 104 may be taller at the back side 120 than at the front side 110, or may be the same height at the front and back. The crotch portion 102 bridges the front and back, extending forward from the rear connecting line 105, and is primarily disposed between the user's legs when the undergarment 100 is worn.

The undergarment 100 may be constructed of any suitable fabric, including plant fibers such as cotton, rayon, viscose, bamboo, hemp, flax, ramie, etc., animal fibers, such as silk or wool, or synthetic fibers, such as nylon, acrylic, polyester, elastane, etc. In a preferred embodiment, the undergarment is constructed of natural fibers, including plant and animal fibers. In a particularly preferred embodiment, the undergarment is constructed of knit cotton fabric, such as knit organic cotton fabric. An example undergarment 100 can be made entirely from a moderately heavy, highly absorbent cotton material. In another embodiment, the crotch piece 200 can be made of a different material than the main body 101, such as to allow better absorption and protection against leakage from incontinence. According to an embodiment, the crotch piece is constructed of an absorbent material and is substantially free of plastic or petroleum based materials. According to another embodiment, the main body of the undergarment is substantially free of plastic or petroleum based materials, with the exception of sewing thread that can be used to sew the undergarment and one or more elastic bands that may be attached to the edges (e.g., around the top and/or the leg openings) of the main body.

In an embodiment, the holding portion 104 can be constructed of an elastic material that is covered with another material, such as a material substantially similar to the material from which the main body 101 is made. The main body 101 can be made using a relatively light, breathable, yet absorbent (e.g., highly absorbent) cotton material. In an embodiment, the undergarment 100, including the crotch piece 200, is made from organic cotton, and the holding portion comprises an elastic material that may be partially or completely covered by the organic cotton. Examples of elastic materials include, for example, rubber, latex, elastane, silicone, and combinations thereof. The elastic material may be provided in any suitable form, such as an elastic band, elastic tape, elastic lace, etc. The crotch piece 200 can be made from denser, more absorbent cotton than the main body 101. The undergarment 100 could be manufactured using a known manufacturing process.

In the embodiments, the undergarment 100, and particularly the crotch piece 200, are constructed to be non-bulky, while being absorbent. The terms "bulky" and "non-bulky" are used here to describe the tendency (or lack thereof) of the undergarment to create excess bulk in the crotch area of the user, particularly between the legs. A bulky undergarment can be not only uncomfortable for the user, but also be visible from the outside through the outer clothing of the user. In an embodiment, the materials (e.g., natural fabrics), thickness of the materials, thickness of the crotch piece 200, and placement of the crotch piece 200 are such that the undergarment 100 is non-bulky and provides the desired absorbency and protection. According to an embodiment, the crotch piece 200 has a thickness of less than 8 mm, less than 6 mm, less than 5 mm, or less than 4 mm. In some embodiments, the crotch piece 200 has a thickness of between about 1 and 6 mm.

Figure 3:
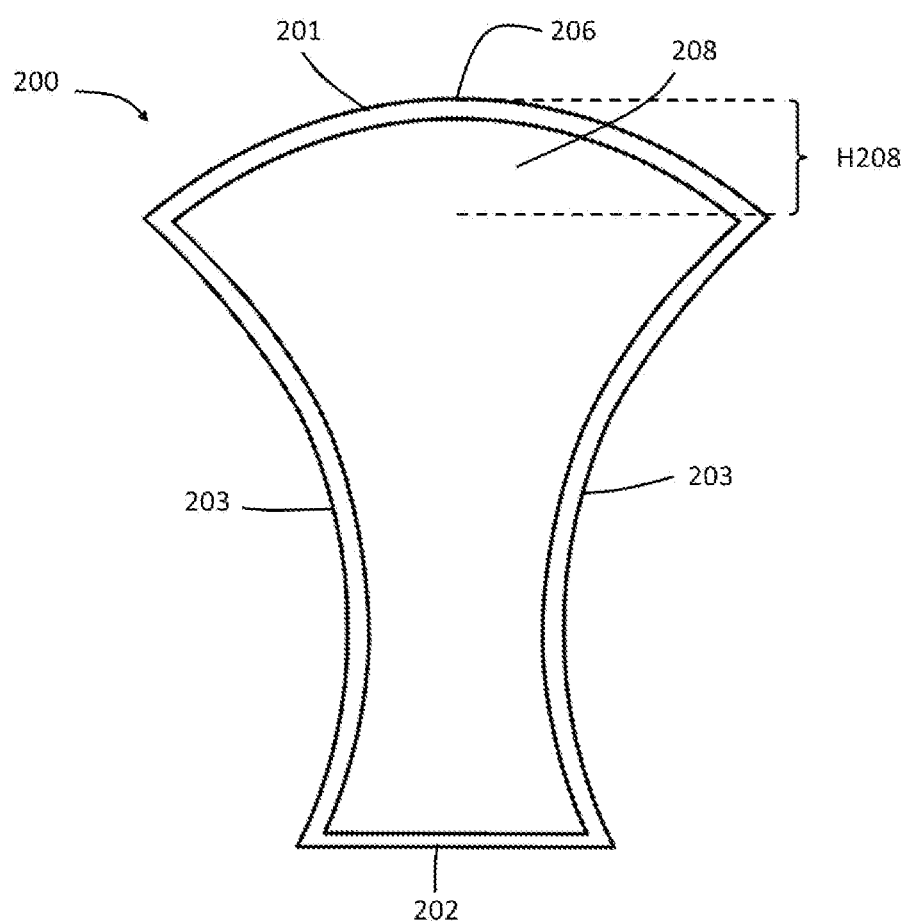
FIG. 3 shows a perspective view of an example of a crotch piece detached from the undergarment's main body.

FIG. 3 shows an embodiment of the crotch piece 200, comprising a first end 201, a second end 202, and sides 203. The second end 202 of the crotch piece 200 can attach to the main body 101 at or near the rear connecting line 105. The connection can continue around the crotch portion 102 so that the crotch piece 200 is substantially attached to the crotch portion 102 at the sides 203 (i.e., attached so as to be firmly secured to the crotch portion 102). This attachment can be achieved through the use of any suitable method, such as sewn seams, an adhesive, or melt adhesion. In a preferred embodiment, the crotch piece 200 is sewn to the main body 101 of the undergarment 100 at the sides 203 of the crotch piece 200. Adjacent to the first end 201, the crotch piece 200 can include a curved portion 208 that extends upward on the front side 110 of the undergarment 100. The curved portion 208 can have an apex 206 at or near the intersection of the curved portion 208 and a vertical midline 109 (see FIG. 1). The apex 206 may extend about 70-250 mm, or about 100-200 mm, or about 120-170 mm toward the front side from a center bottom fold line 103. The center bottom fold line 103 can be established when the undergarment 100 is laid flat with the top of the front side 110 aligned with the top of the back side 120.

In the embodiments, the undergarment 100 is constructed to provide full protection against leaks due to mild or moderate incontinence, while being comfortable, non-bulky and inconspicuous. This can be achieved by using a non-bulky crotch piece 200 and by the correct placement and size of the crotch piece 200. According to some embodiments, the top edge or the apex 206 of the crotch piece 200 extends between about 100 to 200 mm, or about 120 to 170 mm from a bottom center fold line. According to some embodiments, the second end 202 of the crotch piece 200 that connects with the rear connecting line 105 extends between about 20 to 100 mm, or about 50 to 80 mm back from the bottom center fold line 103.

The crotch portion 102 is a section of the main body 100 intended to be disposed between the legs of the wearer when the undergarment 100 is in use.

Figure 2:
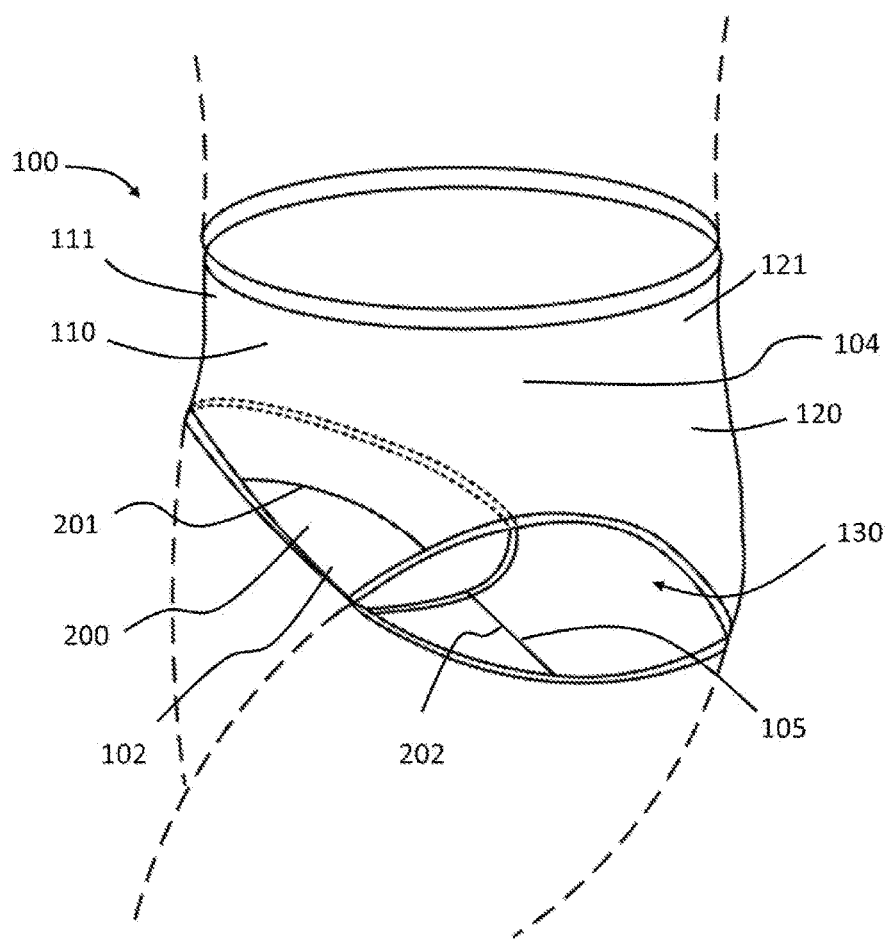
FIG. 2 shows a perspective view of an example of an incontinence undergarment worn by a person.

FIG. 2 is a perspective view diagram of the example undergarment 100. A brief-style undergarment is shown. The undergarment 100 includes a main body 101 (having a crotch portion 102, and a holding portion 104) and a crotch piece 200 coupled with the crotch portion 102. The holding portion 104 can be made from an elastic material (such as a knit fabric, a material comprising an elastic, and/or an elastic band), so as to facilitate securing the undergarment 100 to a user's body. To ensure protection against leaks, the leg holes 130 can be configured to have an improved fit. For example, it may be desirable to have leg holes 130 with a snug fit. In a preferred embodiment, the leg holes 130 have a comfortable yet snug fit. A comfortable yet snug fit can be understood to mean leg holes 130 that fit against the body of the wearer without excess fabric, for example in an undergarment constructed with negative ease. The width of the crotch portion 102, as well as the distance between line 107 and the bottom fold line 103, the circumference of the leg holes 130, and the elastic material and the length of the elastic material used at the leg holes 130, can determine the fit of the leg holes 130. A wider crotch portion 102, or shallower and/or narrower leg openings result in a closer, more secure fit upon a user's body when worn. This secure fit can help to prevent bodily fluids from leaking out of the undergarment 100. The width of the crotch piece 200 can be matched to the width of the crotch portion 102.

Figure 4A:
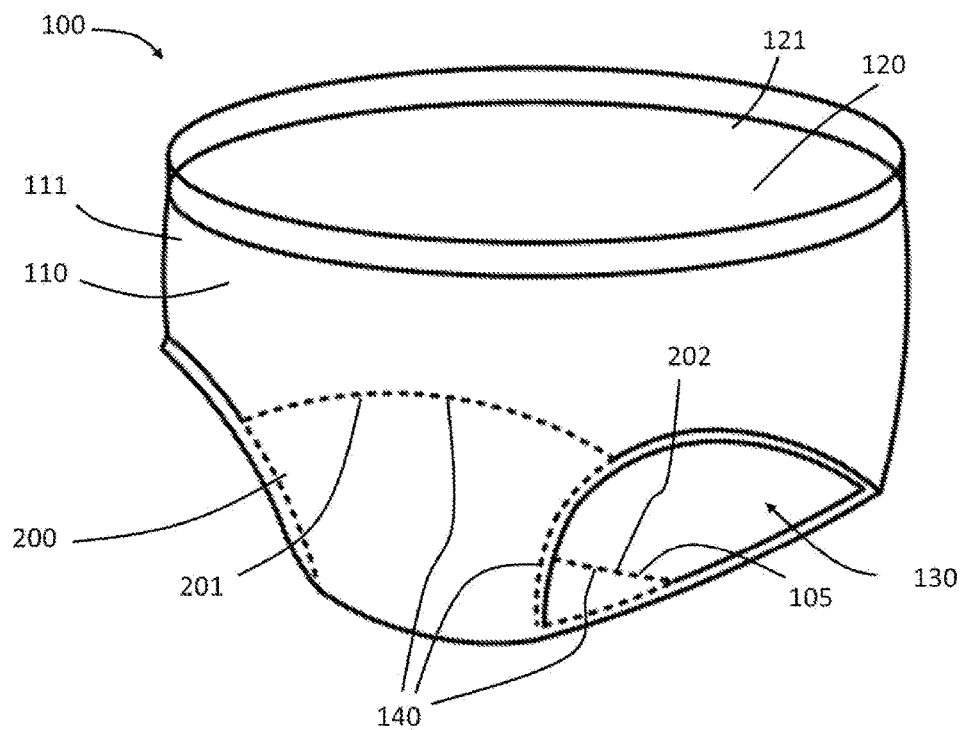
FIGS. 4A and 4B show perspective views of an example of an incontinence undergarment with the crotch piece detached from the undergarment's main body.

As shown in FIGS. 3 and 4A, the crotch piece 200 can include a curved portion 208 at the first end of the crotch piece 200 that is positioned at the front side 110 of the main body 101 and extends toward the holding portion 104 of the main body 101. In an embodiment, the crotch piece is positioned primarily on the front side 110 of the undergarment. The second end 202 of the crotch piece 200 can be connected to the rear connecting line 105 of the main body 101. The sides 203 of the crotch piece 200 can be curved to match the curve of the crotch portion 102 of the main body 101. The sides 203 can be attached to the crotch portion 102 at the leg holes 130. The crotch piece 200 can be of any suitable width. The width at the first end 201 can be such that it provides protection against leaks. In one embodiment, the width at the first end 201 is similar to or about the same as the width of the main body 101 at the line where the first end 201 meets the main body 101. The width at the second end 202 can be such that it allows substantial attachment to the rear connecting line 105 of the main body 101. If the second end 202 is made wider, there will be an increase in the area of protection offered by the undergarment 100. The crotch piece 200 extends from the rear connecting line 105, past the center fold line 103, toward the upper portion 111 of the front side 110. In an embodiment, the crotch piece 200 extends part of the way onto the upper portion 111 of the front side 110. Such a configuration can help protect against leaks due to incontinence. An increase in the surface area of the crotch piece 200 can help protect from spotting and leakage that occur between the center fold line 103 and the first end 201 of the crotch piece 200 (shown in FIG. 1). According to an embodiment, the width of the second end 202 can be about 7 to about 160 mm, or about 100 to about 150 mm. At its widest point (at the first end 201 or at the curved portion 208), the crotch piece 200 can be about 120 to about 250 mm, or about 140 to about 200 mm wide. The height H208 of the curved portion 208 (measured vertically from the line of its widest point to the apex 206) can be about 5 to about 70 mm, or about 20 to about 60 mm. In an exemplary embodiment, the second end 202 is about 140 mm wide, the apex 206 of the curved portion 208 is about 200 mm from the second end 202, the width of the curved portion 208 at its widest point is about 200 mm, and the height H208 of the curved portion is about 40 mm. Other sets of dimensions are contemplated in this disclosure. It will be appreciated by those skilled in the art that the measurements of the crotch piece 200 will vary depending on the size of the undergarment (e.g., small, medium, or large).

Figure 4B:
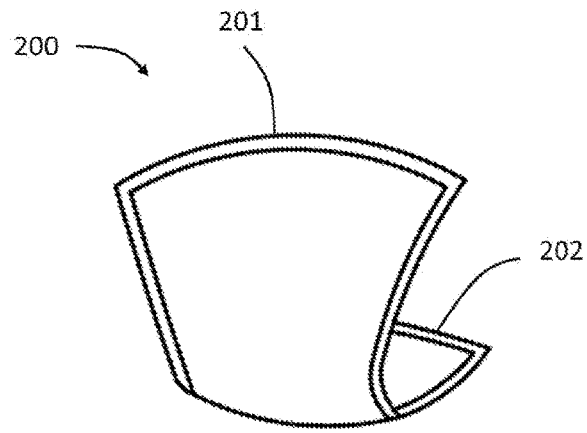

FIGS. 4A & 4B show a perspective view of the undergarment 100 and crotch piece 200. The location of the crotch piece 200 is outlined in FIG. 4A via dotted lines. FIG. 4B shows the crotch piece 200 independent of the rest of the undergarment 100. The undergarment comprises a crotch piece 200 that is attached to a main body 101 by sewn seams. The undergarment 100 can include one or more finished seams 140. The finished seams 140 can be located where the crotch piece 200 and crotch portion 102 are attached on the main body 101. A finished seam can be made using a French seam or other seaming technique that leaves no raw fabric edges exposed. A finished seam 140 can be more comfortable than an unfinished seam (e.g., not as "scratchy") on the skin of a person wearing the undergarment 100.

Figure 5:
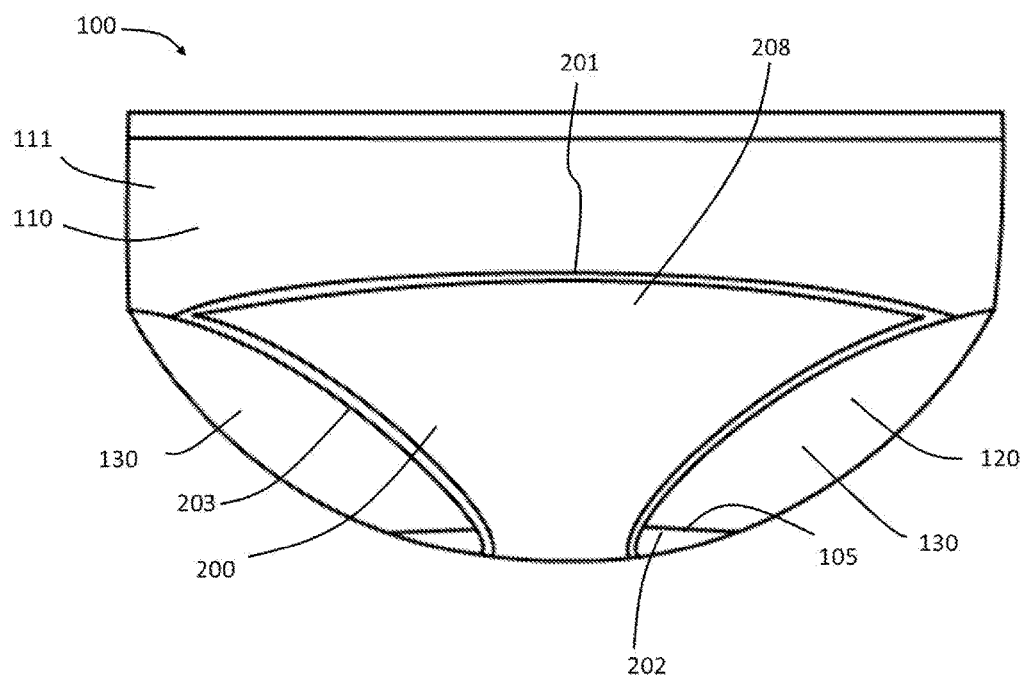
FIG. 5 shows a front view of an example of an incontinence undergarment.
Figure 6:
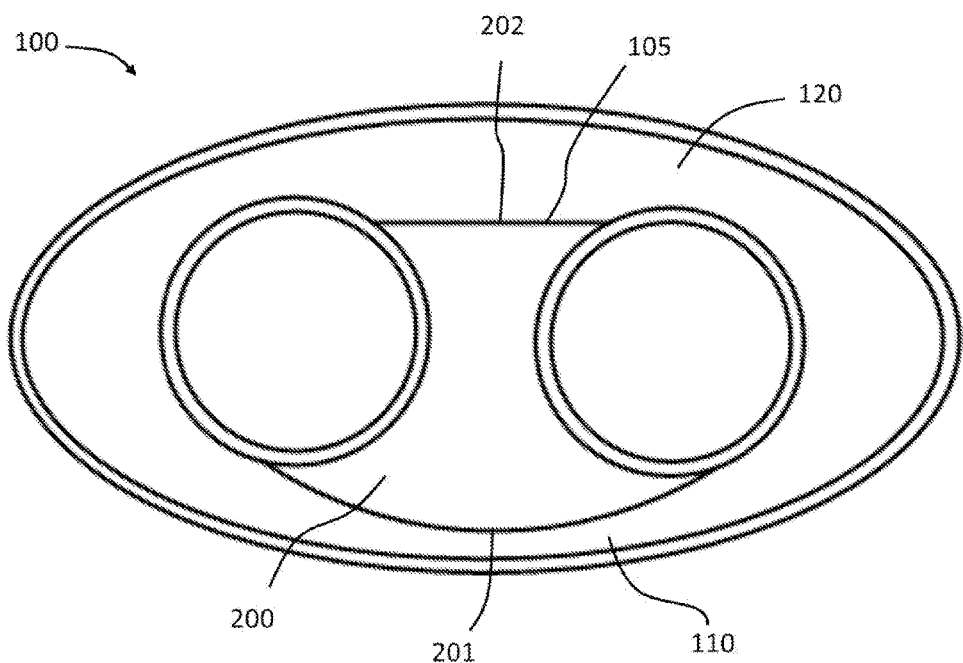
FIG. 6 shows a top view of an example of an incontinence undergarment.

FIGS. 5 and 6 show a front view and a top view of the undergarment 100, respectively. The undergarment 100 includes a main body 101 with a front side 110 and a back side 120, a crotch portion 102, and a crotch piece 200 coupled to the main body 101. The crotch portion 102 and the crotch piece 200, in combination, can extend to the upper portion 111 of the front side 110. This extension can help ensure that leaked bodily fluids will be caught and contained in the area that is covered by the crotch portion 102 and the crotch piece 200. The sides 203 of the crotch piece 200 that are contiguous with the leg holes 130 can remain uncoupled from the crotch portion 102 (e.g., unsewn or otherwise unattached to the main body 101). In such an embodiment the crotch piece 200 can be connected to the crotch portion 102 at the curved portion 208 along the first end 201 and the rear connecting line 105. Such an embodiment can allow additional incontinence protection, such as a sanitary napkin, pad, or other suitable incontinence protection device, to be inserted between the crotch portion 102 and the crotch piece 200.

One or more embodiments discussed herein may include fewer features than illustrated or discussed. The embodiments described herein are not meant to be an exhaustive presentation of the ways in which the various features of the invention may be combined. Accordingly, the embodiments are not mutually exclusive combinations of features; rather one or more embodiments may include a combination of different features selected from different individual embodiments discussed.

EXAMPLES

Example 1

Various forms of protective undergarments were tested and evaluated on a number of parameters. Samples were obtained from Dear Kate®, available from Dear Kate, Inc. in New York, N.Y.; Wearever®, available from Prime Life Fibers, Inc., in Durham, N.C.; Depend®, available from Kimberly-Clark Corp., in Neenah, Wis. Dear Kate and Wearever products were manufactured out of various fabrics. The Depend-brand products were paper-based disposable products. Sample 10 was an exemplary embodiment according to the present disclosure. The parameters included: comfort, softness, pliability of the absorbent pad, bulk, quietness, positioning of the pad, and fit in the front and back and overall fit.

Results of the testing are shown in TABLE 1 below.

TABLE 1

| | Comfort | Softness | Pliability of pad | Bulk | Quietness | Positioning of pad | Fit Front | Back | Overall |
|---|---|---|---|---|---|---|---|---|---|
| Sample 1 (Dear Kate 1) | 4 | 4 | 5 | 5 | 5 | 4 | 3 | 0 | 2 |
| Sample 2 (Dear Kate 2) | 4 | 4 | 5 | 5 | 5 | 4 | 4 | 0 | 2 |
| Sample 3 (Dear Kate 3) | 3 | 4 | 5 | 4 | 5 | 3 | 3 | 0 | 1 |
| Sample 4 (Wearever 1) | 1 | 3 | 2 | 2 | 2 | 3 | 2 | 1 | 2 |
| Sample 5 (Wearever 2) | 1 | 3 | 1 | 2 | 2 | 2 | 2 | 1 | 1 |
| Sample 6 (Wearever 3) | 1 | 2 | 1 | 2 | 1 | 3 | 2 | 1 | 2 |
| Sample 7 (Wearever 4) | 2 | 3 | 1 | 1 | 2 | 2 | 3 | 1 | 2 |
| Sample 8 (Depend 1) | 1 | 1 | 1 | 1 | 1 | 1 | 1 | 1 | 1 |
| Sample 9 (Depend 2) | 2 | 1 | 1 | 1 | 1 | 1 | 2 | 1 | 1 |
| Sample 10 (Exemplary embodiment) | 5 | 5 | 5 | 5 | 5 | 5 | 5 | 5 | 5 |

It was determined that each of the tested currently commercially available protective underwear (Dear Kate, Wearever, and Depend) was lacking on one or more of the tested parameters. Sample 10, which was prepared according to the parameters of the present disclosure, was found to be comfortable, non-bulky, and quiet, with a pliable pad that was positioned correctly for preventing leaks resulting from mild to moderate incontinence. The fit of Sample 10 was superior both in the front, back, and overall.

In Example 2, the undergarment can include a crotch piece that rests partially between the leg holes, wherein the crotch piece is at least partially connected to the crotch portion of the main body at the rear connecting line, and wherein the crotch piece extends between about half way and all the way to the lower edge of the holding portion from the rear connecting line.

In Example 3, the undergarment of Example 2 can include a crotch piece that rests partially between the leg holes, wherein the crotch piece is disposed on the outer side of the main body and is at least partially connected to the crotch portion of the main body at the rear connecting line, and wherein the crotch piece extends between about half way and all the way to the lower edge of the holding portion from the rear connecting line.

In Example 4, the undergarment of Example 2 can include first and second crotch pieces that rest partially between the leg holes, wherein the first crotch piece and second crotch pieces are disposed on an inner side of the main body, and wherein the pair of crotch pieces are at least partially connected to the crotch portion of the main body at the rear connecting line, and wherein the crotch piece extends between about half way and all the way to the lower edge of the holding portion from the rear connecting line. This triple layer of protection can also be achieved if one of the crotch pieces is disposed on the outer side of the main body.

In Example 5, the main body, the crotch portion, and the crotch piece of at least one of Examples 2-4 are made of a material that allows absorption of fluids.

In Example 6, the portion of the crotch piece extending between about half way and all the way to the lower edge of the holding portion from the rear connecting line of at least one of Examples 3-5 has an arc with an apex located at the midline of the undergarments main body.

In Example 7, the crotch piece of at least one of Examples 3-6 is made of different material than the main body.

In Example 8, the crotch portion of at least one of Examples 2-7 is made of different material than the remainder of the main body.

In Example 9, the undergarment of at least one of Examples 3-8 includes an absorbent article inserted between the crotch portion and crotch piece (e.g., the first or second crotch piece).

In Example 10, the main body of at least one of Examples 2-9 includes finished seams.

What is claimed is:

1. An undergarment, comprising:
   a main body comprising two leg holes, a front side and a back side connected at a bottom center fold line, a holding portion comprising an upper portion of the front side and an upper portion of the back side, a crotch portion resting between the two leg holes and bridging the upper portions of the front side and the back side, wherein the crotch portion connects with the upper portion of the back side at a rear connecting line; and
   a crotch piece that rests at least partially on the crotch portion, wherein the crotch piece at second end is at least partially connected to the crotch portion of the main body at the rear connecting line, and wherein the crotch piece extends from the rear connecting line to the front side, extending a part of the way onto the upper portion of the front side, wherein an apex of the crotch piece is closer to the front side waist line compared to the bottom center fold line and wherein the second end is closer to the bottom center fold line compared to the back side waist line and,
   wherein the crotch piece is constructed of an absorbent material and is substantially free of plastic, and wherein the undergarment, comprising the main body and the crotch piece, is machine washable and reusable.

2. The undergarment of claim 1, wherein the main body is constructed of an absorbent material and is substantially free of plastic materials.

3. The undergarment of claim 1, wherein the undergarment further comprises one or more elastic bands coupled with the main body at one or more edges of the main body.

4. The undergarment of claim 3, wherein the undergarment is substantially free of plastic materials except for the one or more elastic bands.

5. The undergarment of claim 1, wherein the crotch piece is constructed of different material than the main body.

6. The undergarment of claim 1, wherein the main body, holding portion, crotch portion, and crotch piece are connected by finished seams.

7. The undergarment of claim 1, wherein the crotch piece comprises a plurality of layers.

8. The undergarment of claim 7, wherein the main body comprises an outer side and an inner side, and wherein one or more of the plurality of layers is disposed on the outer side of the main body with the balance disposed on the inner side.

9. The undergarment of claim 7, wherein the crotch piece has a thickness of less than 6 mm.

10. The undergarment of claim 1, wherein the crotch piece extends to between about 100-200 mm on the front side from the bottom center fold line.

11. The undergarment of claim 1, wherein the crotch piece extends to between about 120-170 mm on the front side from the bottom center fold line.

12. The undergarment of claim 1, wherein the crotch piece extends to between about 20-100 mm on the back side from the bottom center fold line.

13. The undergarment of claim 1, wherein the crotch piece extends to between about 50-80 mm on the back side from the bottom center fold line.

14. The undergarment of claim 1, wherein the undergarment comprises a brief.

15. The undergarment of claim 1, wherein the undergarment is substantially constructed of organic cotton knit fabric.

16. The undergarment of claim 1, wherein the undergarment is substantially free of petroleum-based materials.

* * * * *